United States Patent
Kasvikis et al.

[11] Patent Number: 5,364,364
[45] Date of Patent: Nov. 15, 1994

[54] AUTOMATIC FLOW CONTROL VALVE SYSTEM

[75] Inventors: Spyros Kasvikis, Escondido, Calif.; Richard W. Herrmann, Raleigh, N.C.; Simon E. Finburgh, San Diego, Calif.

[73] Assignee: IVAC Corporation, San Diego, Calif.

[21] Appl. No.: 101,988

[22] Filed: Aug. 4, 1993

[51] Int. Cl.$^5$ .................................... A61M 1/00
[52] U.S. Cl. ................................. 604/151; 604/131; 604/32; 604/248; 137/556
[58] Field of Search ................. 604/30, 32, 131, 151, 604/246, 248; 137/556; 251/209, 288

[56] References Cited

U.S. PATENT DOCUMENTS

| | | | |
|---|---|---|---|
| 3,097,585 | 7/1963 | Carlson | 95/89 |
| 3,831,625 | 8/1974 | Roediger | 137/377 |
| 3,858,601 | 1/1975 | Ensinger | 137/374 |
| 3,957,082 | 5/1976 | Fuson et al. | 137/625.41 |
| 4,460,358 | 7/1984 | Somerville et al. | 604/250 |
| 4,557,725 | 12/1985 | Heyne et al. | 604/151 |
| 4,585,411 | 4/1986 | Archibald | 604/245 |
| 4,585,442 | 4/1986 | Mannes | 604/250 |
| 4,689,043 | 8/1987 | Bisha | 604/250 |
| 5,005,604 | 4/1991 | Aslanian | 604/32 |
| 5,017,192 | 5/1991 | Dodge et al. | 604/250 |
| 5,156,186 | 10/1992 | Manska | 137/556 |
| 5,219,327 | 6/1993 | Okada | 604/34 |
| 5,244,463 | 9/1993 | Lorcher et al. | 604/151 |

Primary Examiner—John G. Weiss
Attorney, Agent, or Firm—Fulwider, Patton, Lee & Utecht

[57] ABSTRACT

A fluid flow control system having a valve disposed in-line with a fluid conduit extending between a fluid container and a fluid receiver. The conduit and valve are designed to be used with a fluid infusion device such as a peristaltic pump. The valve is non-clamping and includes a rotatable member with an external handle for controlling the valve between flow and flow stop positions. The handle can be manually operated as well as automatically operated. Mounted to the infusion device is an automatic operating mechanism for cooperating with the pumping mechanism of the infusion device to control the position of the valve. In a disclosed embodiment, the operating mechanism is mounted to an access door of the pump which cannot be closed until the peristaltic mechanism is engaged with the tubing. When the door is closed, the operating mechanism automatically moves the valve to the flow position. When the access door is opened, the mechanism automatically moves the valve to the flow stop position. The pumping mechanism cannot be disengaged from the tubing without first opening the access door, which automatically closes the valve as described above. In one embodiment, the access door includes a retractor arm and a block for selectively operating the valve handle.

28 Claims, 5 Drawing Sheets

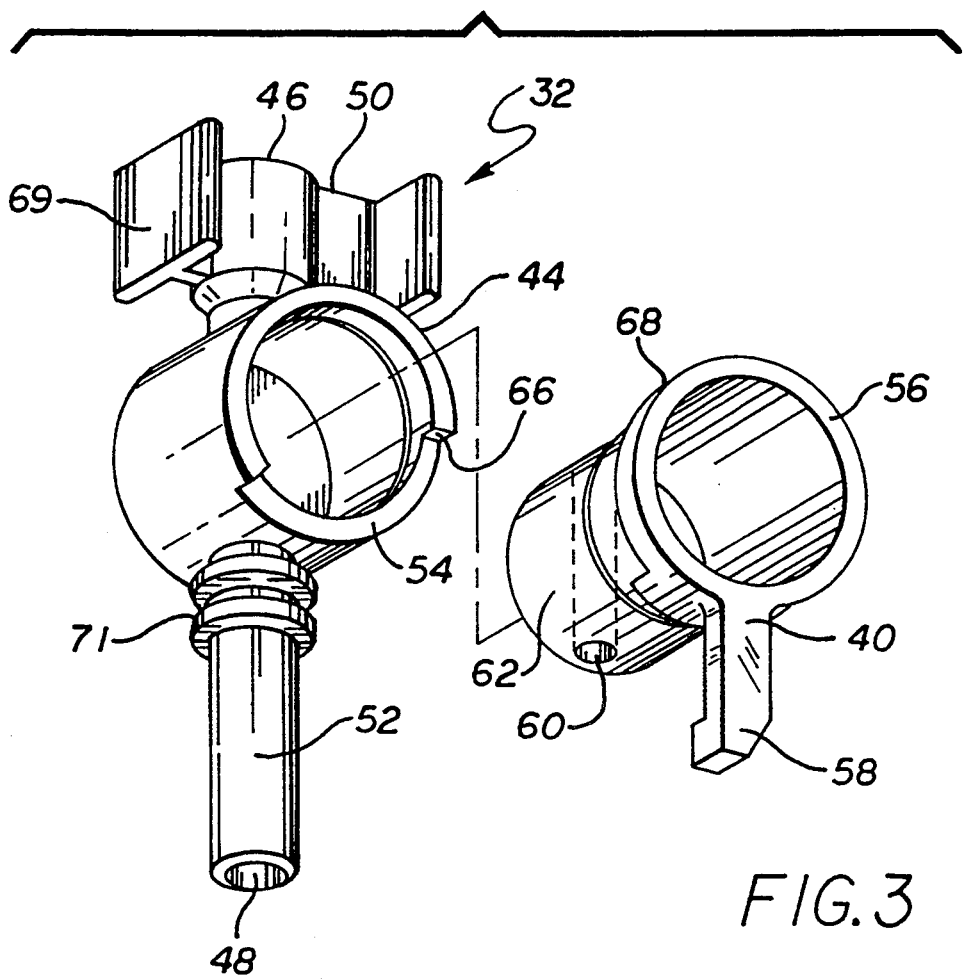
FIG. 3
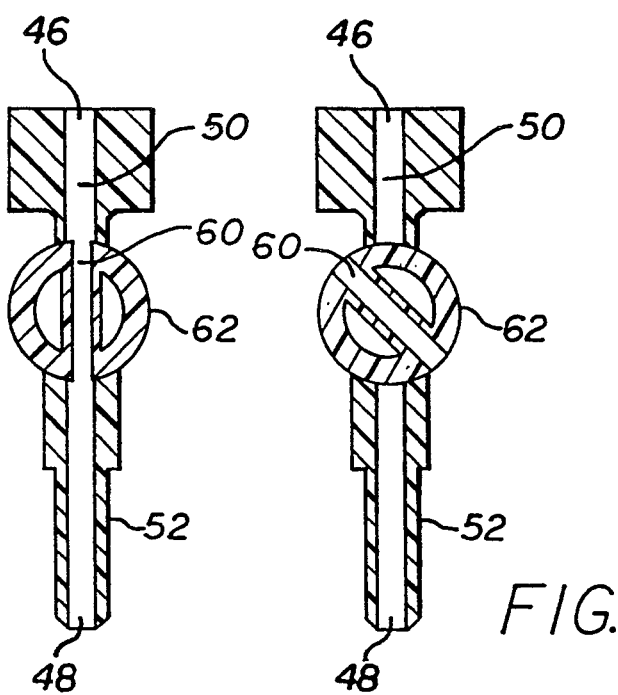
FIG. 4
FIG. 5

AUTOMATIC FLOW CONTROL VALVE SYSTEM

BACKGROUND

The invention relates generally to improvements in fluid flow control systems and, more particularly, to a valve which is operated in cooperation with an infusion device.

In many cases where a fluid containing medication located in a reservoir is infused into the vascular system of a patient through a fluid conduit and cannula, a volumetric flow control device, such as a peristaltic pump, is used to precisely control the infusion of that fluid. The pump operates on the conduit to control the infusion process so that the prescribed amount of the medication is infused in accordance with the therapy schedule. In the cases of some medications, they are most effective when specific amounts are administered over a certain time period. The administration of a lesser or an excess amount may not achieve the desired therapeutic effect with that medication. Additionally, the administration of an excess amount may have an adverse effect on the patient because of the condition of the patient and the characteristics of the medication. Thus, control over the flow of IV fluid to the patient is a significant concern.

With devices such as peristaltic pumps which mechanically operate on the conduit to control flow, flexible tubing is included in the conduit connecting the fluid container with the cannula. Typically, a separate, manually-operated flow stop device located upstream from the pump is used to prevent the free flow of the fluid through the tubing when the pump is not engaged with the tubing. The flow stop device is manually operated to mechanically pinch off the tubing thereby preventing the flow of fluid.

In operation, the tubing is connected to the reservoir with the manual flow stop open so that air is discharged from the tubing by the flow of fluid through it from the reservoir. The manual flow stop is then engaged to pinch the tubing closed at an upstream position so that no flow can occur. The tubing is properly installed in the pump downstream from the manual flow stop and is coupled to the patient. It is common practice to design peristaltic pumps such that no direct fluid flow path exists through the pump from the fluid reservoir to the patient. The tubing is always occluded by one or another mechanism of the pump at all times. For example, the pumping mechanism may be designed to provide continual occlusion of the tubing. The tubing may be occluded against a pressure plate by at least one of the peristaltic fingers when the pump is placed in its operational configuration. In some cases, such pumps have doors, levers, or other mechanisms which interact with the pumping mechanism to control its engagement with the tubing. For example, when moved in one direction, such a lever causes the pressure plate of a peristaltic mechanism to be moved away from the peristaltic fingers so that the tubing can be installed between the two. By moving the lever in the opposite direction, the pressure plate is moved to engage the tubing with the peristaltic fingers thereby placing the pumping mechanism in its operational configuration whereby at least one finger occludes the tubing.

In one case, an engagement lever controls engagement of the peristaltic mechanism with the tubing as described above; however, an access door is also included with the pump. The access door provides protection for the peristaltic mechanism and other components and must first be opened to either install or remove the tubing. Additionally, a magnetically or otherwise activated switch may be used to determine if the access door is closed and the pump will not operate until the magnetic switch senses closure of the door. In some cases, the door and engagement lever may be coupled together so that movement of the door is separate from movement of the engagement lever; that is, they are separate actions. In other cases, movement of the door may cause movement of the lever.

In other cases, the peristaltic mechanism may be pivotally mounted and movement of a tubing access door causes the peristaltic mechanism to pivot away from a stationary pressure plate so that the tubing can be installed. Closing the door after the tubing has been installed causes the peristaltic mechanism to pivot towards the pressure plate and engage the tubing thereby entering the operational configuration.

After installing the tubing in the pump, engaging the pumping mechanism with the tubing, and closing the access door, the upstream manual flow stop device is released from pinching off the tubing. The pump now provides the control over the flow of fluid in the fluid line and even though not operating, is occluding the tubing to prevent the free flow of the fluid.

The pump may be programmed to administer a predetermined amount of the infusion fluid to the patient over a particular time period and then stop pumping and provide a prompt. This predetermined amount of infusion fluid may be less than the amount of fluid in the fluid reservoir and in such a case, fluid will remain in the tubing and in the reservoir after the pump stops. It is normal practice after infusion is complete for the operator to close the upstream manual flow stop thereby pinching off the tubing before disengaging the pumping mechanism from the tubing. Failure to manually pinch off the tubing before opening the pump may allow the free flow of the remaining fluid into the patient because the pump is no longer occluding the tubing. As discussed above, this free flow of additional fluid would not be in accordance with the therapy schedule. It would be desirable in such infusion arrangements to assure that the flow is shut off before the pump is disengaged.

Prior attempts have been made to automatically engage and disengage a tubing clamp in conjunction with the positioning of the peristaltic mechanism. However, the use of a tubing clamp results in physical deformation of the tubing to achieve occlusion and this occluding deformation may leave a permanent deformation in the tubing depending upon how long the tubing is held in the compressed condition by that clamp and how much compressive force is applied. Additionally, failure to properly design such a clamp may even result in permanent deformation of the tubing. Such a result may occur if the clamp exceeds the mechanical limits of the tubing during operation. Permanent deformation of the tubing can impede the flow of fluid to the pump and compromise the ability to maintain high flow rates. Such a result is undesirable.

Hence, those concerned with the infusion of fluids into patients, and particularly, those concerned with flow control devices such as peristaltic-type pumps, have recognized the need for an improved, relatively simple, more economical, durable, and reliable system for preventing the free flow of fluid through a fluid conduit. Those concerned have also recognized the desirability of providing a flow stop system which is interactive with the pumping mechanism so that engagement of the flow stop occurs to shut off the flow before the pumping mechanism is disengaged from the conduit. The present invention fulfills these needs and others.

SUMMARY OF THE INVENTION

Briefly and in general terms, the invention is directed to an apparatus for controlling the flow of fluid through a conduit which is operated on by a fluid infusion device to infuse a medical fluid to a patient. The apparatus comprises a valve disposed in line with and in fluid communication with the conduit such that fluid flowing through the conduit flows through the valve. The valve has a passage through which the fluid may flow, a movable flow control member mounted in the valve being movable into a first position in which the flow control member is disposed in the passage to block flow through the passage, and a second position in which the flow control member does not block flow through the passage. Additionally, an infusion engagement member has an engaged position at which it controls the fluid infusion device to engage the conduit for infusing fluid to the patient and having a disengaged position at which the infusion engagement member controls the fluid infusion device to be disengaged from the conduit. The apparatus also includes a positioning device mounted to the fluid infusion device which controls the position of the flow control member and which interacts with the infusion engagement member so that the positioning device is restricted from setting the flow control member to the second position until after the infusion engagement member is in the engaged position.

In a further feature in accordance with the invention, the positioning device comprises a retractor arm which engages the flow control member to move the flow control member to the first position when the positioning device is moved in a first direction and a block which engages the flow control member to move the flow control member to the second position when the positioning device is moved in a second direction. In one case, the positioning device is mounted to an access door of the infusion device. The access door has open and closed positions and the positioning device is mounted to the access door such that when moving the access door from the open position to the closed position, the second member of the position device engages the flow control member to move the member into the second position and when moving the access door from the closed position to the open position, the first member of the positioning device engages the flow control member to move the member to the first position.

In another feature of the invention, the movable flow control member includes a handle which controls the position of the flow control member and has first and second positions corresponding to the first and second positions of the flow control member. The retractor arm is mounted to the access door and engages the handle to move the handle to the first position when the access door is moved from the closed to the open position and the block is also mounted to the access door and engages the handle to move the handle to the second position when the access door is moved from the open to the closed position.

In a further aspect, the upper surface of the handle is ramp shaped to guide the retraction arm into position. Additionally, the end of the handle is rounded for facilitating its movement when contacted by the block.

In yet a further aspect in accordance with the invention, the movable flow control member comprises a rotatable member inserted in the passage, the rotatable member having a channel which when aligned with the passage permits the flow of fluid through the valve and which when misaligned with the passage blocks the flow of fluid through the valve, the first position having the channel misaligned with the passage and the second position having the channel aligned with the passage.

In further features of the invention, the infusion engagement member can only be accessed after the positioning device has moved the flow control member to the first position. Additionally, the positioning device interacts with the infusion engagement member so that the positioning device moves the flow control member to the first position before the infusion engagement member can be moved to the disengaged position.

Other aspects and advantages of the invention will become apparent from the following detailed description and accompanying drawings, illustrating by way of example the features of the invention.

BRIEF DESCRIPTION OF THE DRAWINGS

FIG. 3 is a perspective drawing of an in-line, non-clamping valve usable in the system of FIG. 2;

FIG. 4 is a cut-away, schematic view of the valve of FIG. 3 having an internal channel located in a flow position;

FIG. 5 is a cut-away, schematic view of the valve of FIG. 3 having an internal channel located in a flow shut off position;

DESCRIPTION OF THE PREFERRED EMBODIMENTS

Figure 1:
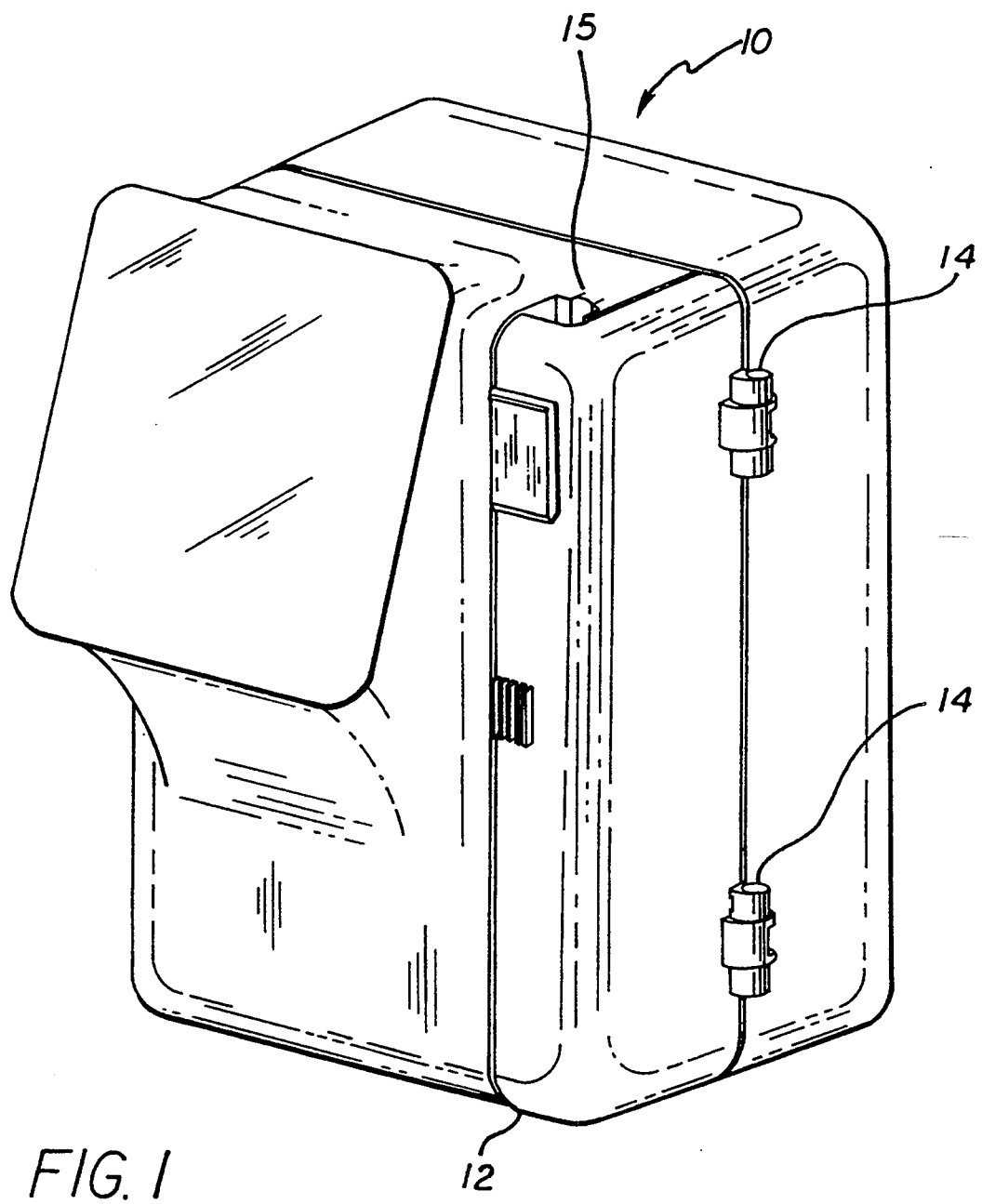
FIG. 1 is a perspective view of a volumetric infusion pump having an access door and incorporating an automatic flow control valve system in accordance with the principles of the invention.

Referring now to the drawings with more particularity, wherein like reference numerals designate like or corresponding elements among the several views, there is shown in FIG. 1 a perspective view of a fluid infusion device which in this embodiment comprises a volumetric fluid infusion pump 10. The pump 10 has an access door 12 through which a fluid conduit, such as a length of flexible tubing (not shown), would be installed to engage the peristaltic mechanism of the pump. The door is hinged 14 in this case. One port 15 through which the conduit would be located is shown.

Figure 2:
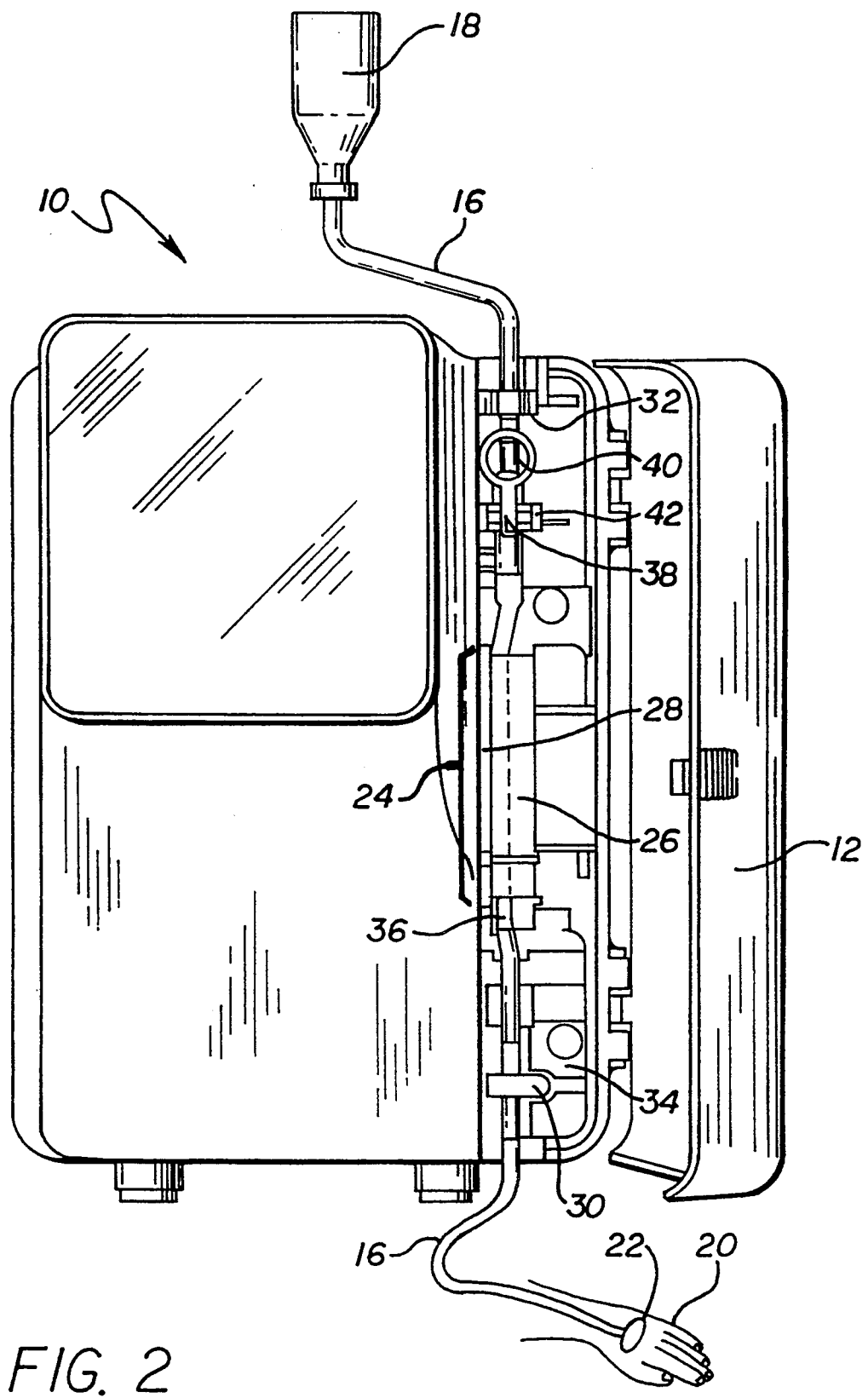
FIG. 2 is a schematic diagram of the pump of FIG. 1 showing the access door open to enable insertion of a fluid conduit. Also shown are the peristaltic mechanism and an in-line flow control valve in accordance with the principles of the invention.

Referring now to FIG. 2, a front view of the pump 10 of FIG. 1 is shown with the access door 12 open. Also shown is a fluid conduit 16 upon which the pump 10 operates to move fluid from a fluid reservoir 18 to a fluid receiver 20, such as the patient shown in the figure. The fluid is delivered to the patient through an inserted cannula 22. The pump 10 of this embodiment comprises a linear peristaltic mechanism 24 which includes a pressure plate 26 for pressing the installed fluid tubing 16 in the direction of the peristaltic fingers 28 with enough force so as to cause occlusion of the tubing 16 with the peristaltic finger or fingers currently engaging the tubing 16. The peristaltic fingers 28 and pressure plate 26 cooperate in the normal manner with the tubing to sequentially occlude the tubing from the upstream end to the downstream end to move fluid from the reservoir 18 to the patient 20.

In FIG. 2, the pressure plate 26 is shown in its released position; i.e., moved away from the peristaltic fingers 28, which enables installation or removal of the tubing 16 in relation to the pump 10. Also shown as part of the tubing 16 for engagement with the pump 10 is an air-in-line sensor adapter 30. The air-in-line adapter 30 is formed as part of the tubing 16 and is shaped to fit securely into a sensor housing 34 containing the required acoustic or other sensors. The tubing 16 also includes an in-line fluid valve 32. Because the fluid valve 32 and adapter 30 are formed in-line with and as part of the tubing 16, and are at opposite ends of the peristaltic mechanism 24, the tubing between them may be formed of a different material than the remainder of the tubing. For example, the segment of the tubing between them may be formed of silicone while the remainder of the tubing 16 may be formed of polyvinyl chloride (PVC).

Also shown in FIG. 2 is an engagement lever 36 for controlling the engagement of the pressure plate 26 with the conduit 16 and the peristaltic fingers 28. When the lever 36 is moved to the right, the pressure plate 26 is moved away from the peristaltic fingers 28 into its released position and the tubing 16 can be installed or removed. When the lever 36 is moved to the left, the tubing 16 is pressed against the fingers 28 for pumping operation. The access door 12 and lever 36 are mounted so that they interact with each other. Because the access door 12 covers the lever 36 when the door 12 is closed, the lever 36 cannot be moved unless the access door 12 is first opened. Because the lever 36 protrudes from the pump 10 when it is in the disengaged position (moved to the right), the access door 12 will strike the lever 36 if the operator attempts to close the access door before moving the lever 36 to the left to engage the pumping mechanism 24 with the tubing 16. However, the access door 12 and lever may be shaped to interact with each other such that when moving the door 12 to the closed position, the door 12 will strike the lever 36 and then continued closure pressure applied to the door 12 will also move the lever 36 to the left thereby engaging the pumping mechanism with the tubing 16 as well as closing the door 12.

Operationally, the access door 12 would be opened, the lever 36 moved to the disengaged position (to the right), the tubing installed between the pressure plate 26 and the peristaltic mechanism 26, the lever 36 moved to the engaged position (to the left) and the access door 12 closed. A magnetic switch (not shown in this figure) indicates that the door 12 is closed and enables the pump 10 to begin pumping fluid. While in this embodiment a separate, manually operable lever 36 is used to control the engagement of the peristaltic mechanism 24 with the tubing 16, other techniques may be used. For example, control over the engagement may be exercised through the position of the access door 12. The door 12 may be coupled to the pumping mechanism such that opening the door 12 will cause the pressure plate 26 to move to its released position and closing the door will cause the pressure plate 26 to engage the tubing 16. In a different embodiment, the door may interact with the peristaltic mechanism itself to move it towards and away from a stationary pressure plate.

The in-line valve or stopcock 32 shown in FIG. 2 has an external handle 38 for placing the valve 32 in a "flow" or a "flow stop" position. As shown, in this embodiment the handle 38 has the shape of a lever which is oriented vertically when the valve 32 is in the flow position. To move the valve 32 to the flow stop position, the handle 38 would be moved to the approximate four o'clock position. Movement of the handle 38 can be performed manually due to the lever shape. Although not shown in the drawings, indicia 40 may be molded into, applied to, or otherwise made a part of the flow control valve or its mounting or surroundings to designate whether the valve is in the "flow" position or in the "flow stop" position. In one embodiment, this indicia may take the form of an arrow molded into the rotating member with the arrowhead pointing in the direction of the handle 38. The pump 10 further comprises a valve receptacle 42 which holds the valve in the desired position for operation. As will be described and shown in greater detail, the positioning of the handle 38 is accomplished by movement of the access door 12 which further interacts with the pumping mechanism.

Turning now to FIG. 3, a view of an in-line valve 32 usable in accordance with the principles of the invention is shown. The valve 32 includes a valve body 44 through which fluid may flow, the body including an input port 46 and an output port 48. Each port 46 and 48 is formed through a fluid tube 50 and 54 respectively which form part of the body 44 of the valve 32. The input tube 50 in one embodiment receives tubing which is slid into it and held in place by adhesive. The output tube 52 is formed so that tubing is slid over it and held in place by friction.

The valve body 44 further includes a central bore 54. This bore 54 is in fluid communication with the input port 46 and the output port 48 thus providing a complete fluid passage through the valve 32. The valve 32 further comprises a rotatable member 56 having a handle 58, a channel 60 formed in the insert portion 62, and indicia 40. The insert portion 62 is positioned inside the bore 54 of the body 44 when the valve 32 is assembled. The orientation of the channel 60 is used to allow flow or stop flow through the valve 32.

Referring now to FIGS. 4 and 5 along with FIG. 3, the effects of alignment and misalignment of the rotatable member 56 and its attached insert portion 62 can more clearly be seen. In FIG. 4, the channel 60 of the insert portion 62 is aligned with the input and output ports 46 and 48 and an unobstructed fluid passage exists and the valve is in the flow configuration. Flow through the valve 32 is not blocked by the rotatable member 56. In FIG. 5, the channel 60 of the insert portion 62 has been rotated approximately 45° and is completely misaligned with the input and output ports 46 and 48. The valve 32 is now in the flow stop configuration. The fluid passage through the valve 32 is therefore blocked. Although shown as a rotation of 45° in FIG. 5, the valve 32 may be designed so that a lesser rotation of the rotatable member 56 will result in complete fluid flow blockage through the valve 32. The rotation of 45° in this embodiment is used as an example only. In another embodiment, a rotation of 20° caused complete misalignment. Positions of the handle 58 in between the aligned and the completely misaligned positions allow control over the volume of fluid flow. This valve design permits manual flow control as well as automatic flow control exercised by the movement of the access door 12 as is discussed below.

Referring again to FIG. 3, stop surfaces 64 and 66 are formed in the body portion 44 to meet with corresponding stop surfaces (not shown) on the rotatable member 56 in a manner well known to those skilled in the art. The rotatable member 56 includes a raised annular ring 68 for retaining the rotatable member 56 in the body portion 44. An annular mounting channel 70 is formed in the valve body 44 to receive the annular ring 68. Additionally, the handle 58 has a ramp shape having a low part on the right side of the handle and the high part on the left side. The distal end of the handle 58 at the low part of the ramp shape is rounded. The purposes of the ramp shape and rounded end are described below.

In one embodiment, the valve body 44 was formed of polycarbonate plastic and the rotatable member 56 was formed of acetal plastic. The insert portion 62 of the valve 32 is pressed into the bore 54 of the body 44.

Figure 6:
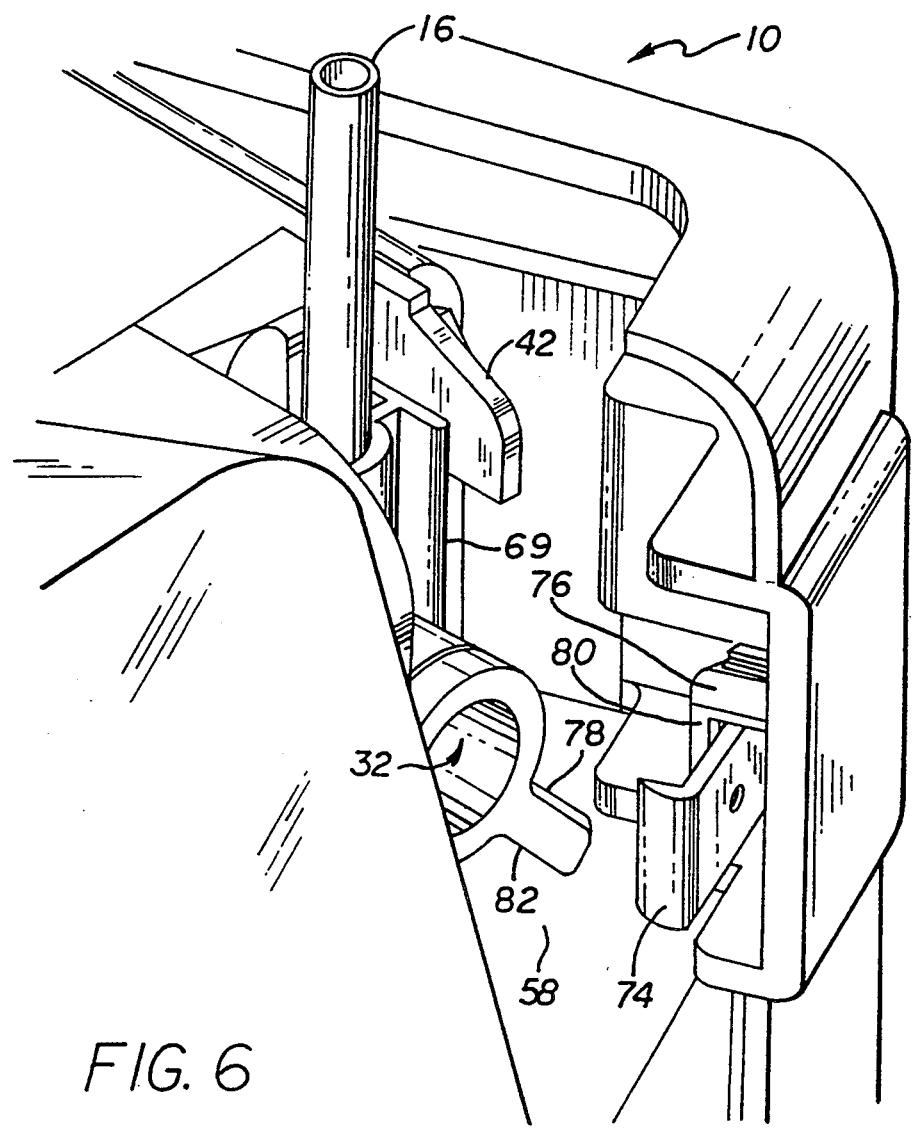
FIG. 6 is a perspective view of the pump of FIG. 2 with its access door partially open and demonstrating the action of the automatic operating mechanism mounted to the access door in relation to the handle of the flow control valve.

Referring now to FIG. 6, the valve 32 is shown mounted in the pump 10 and an automatic operating apparatus 72 is shown for properly positioning the handle 58 of the valve 32. In this case, the automatic operating apparatus 72 comprises a retractor arm 74 and a pushing block 76. The retractor arm 74 is mounted so as to engage the handle 58 of the valve 32 and automatically pull the handle 58 into the flow stop position when the door 12 is opened. The pushing block 76 is mounted in the door 12 so as to engage the handle 58 and to automatically push the handle into the flow position as the door 12 is closed.

Figure 7:
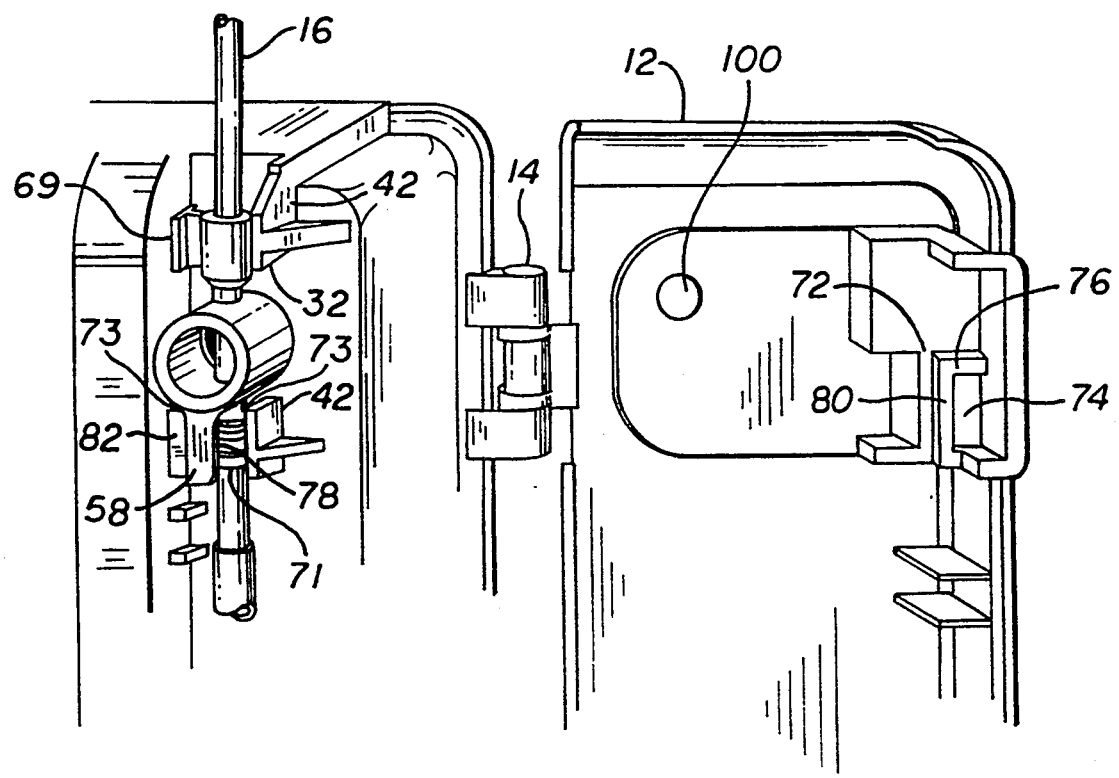
FIG. 7 is a perspective view of the door and pump of FIG. 6 showing the access door completely open.

Referring now also to FIG. 7, the operation of the automatic operating apparatus 72 is shown. The retractor arm 74 and pushing block 76 are mounted to the hinged door 12 so that the operation of the valve 32 can be controlled by the positioning of the door 12. When closing the door 12, the pushing block 76 will encounter a first side 78 of the handle 58 and push the handle 58 towards the vertical or flow position. This can best be seen by reference to FIG. 6. The pushing block in this embodiment comprises two surfaces 76 and 80 which are at right angles to each other. Both will contact the handle 58 as the door 12 is closed. As the door 12 is closed, the pushing block 76 will make contact with the first side 78 of the handle 58 and move it towards the vertical position. Because the door is hinged, the pushing block 76 will encounter the handle 58 out of the plane of the handle at some angle dependent upon the position and distance of the hinges from the handle. The distal end of the handle is rounded 71 as shown in FIG. 5. The rounding of this surface results in smoother operation as the surfaces meet and apply pressure to each other. The rounding has a guiding effect in that it provides less resistance against movement of the contacting components in their desired directions. As shown in FIG. 7, the handle 58 is in the vertical or flow position. When the door 12 is closed with the handle in this position, the pushing block 74 will not make contact with the handle 58.

In opening the door, the retractor arm 74 will engage a second side 82 of the handle 58, in this case opposite the first side 78, and pull the handle 58 into the flow stop position before the arm 74 loses contact with the handle 58. Because the retractor arm 74 must make contact with the second surface 82 of the handle 58, it must bend out of the way when the door is being closed so that it can slide over the front surface of the handle 58 and then snap into position with the second side 82 of the handle once the door 12 is closed. For this purpose, the end of the retractor arm 74 is rounded and the lever part of the handle 58 is ramp shaped as shown in FIG. 5. Also, the arm is mounted in cantilever fashion as is shown and described in more detail below so that bending is facilitated.

In another embodiment, the retractor arm 74 may be hinged to the door and spring loaded towards the handle 58 of the valve 32.

In a further feature, the arm 74 must also bend towards the front of the pump 10 when the arm 74 has moved the handle 58 to its flow stop position and the door 12 continues to be moved to the fully open position. At such point, the continued application of force to the door will cause the retractor arm 74 to bend and release the handle 58.

Referring again to the mounting of the valve 32 in the infusion device, FIG. 3 shows the upper mounting flanges 69 or "wings" for use in mounting the valve 32 in the valve receptacle 42 shown in FIG. 2. As shown more clearly in FIG. 7, the valve receptacle 42 includes an upper part for receiving the upper valve flanges 69 and a lower part for receiving a second set of flanges 71 formed lower on the valve 32. The upper flanges 69 assist in locating and restraining the valve rotationally about the longitudinal axis of the valve so that it does not twist but is properly positioned so that the retractor arm 74 and block 76 can engage the handle 58. The lower flanges rest on shoulders 73 formed on the infusion device for assisting in locating and restraining the valve longitudinally in the infusion device 10. FIG. 6 shows one of the upper flanges 69 correctly mounted in one of the upper parts of the valve receptacle 42.

Figure 8:
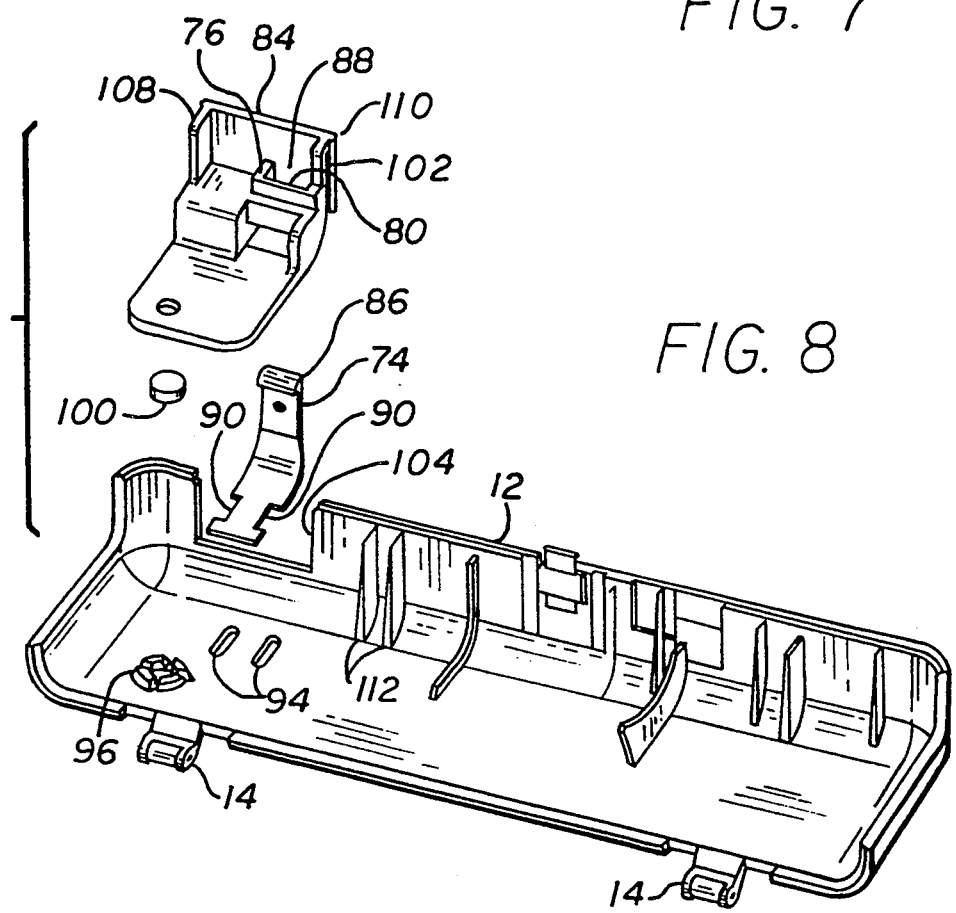
FIG. 8 is an exploded view of the door of the pump of FIG. 7 showing the automatic operating apparatus for the valve.

Turning now to FIG. 8, a view of the access door 12 is shown. The automatic operation apparatus 72 comprises the pushing block bracket 84 and the retractor arm 74. The rounded distal end 86 of the arm 74 can be clearly seen. The bracket 84 includes an opening 88 through which the retractor arm 74 is located during assembly. The retractor arm 74 also includes slots 90 for accepting protrusions 92 formed on the bottom of the bracket 84 which are best seen by reference to FIG. 9. Slots 94 have been formed in the door 12 to accept the protrusions 92 of the bracket 84 thereby accurately locating the bracket 84 and the retractor arm 74 in relation to both the door 12 and to each other.

Figure 9:
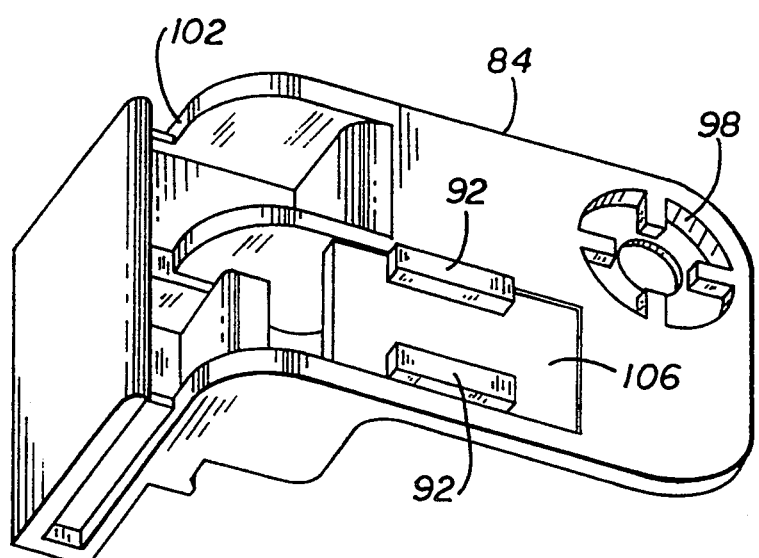
FIG. 9 is a perspective bottom view of the bracket of FIG. 8.

Further facilitating the accurate location of the retractor arm 74, the bracket 84 and the door 12 with each other is the slotted, raised ring 96 formed on the door 12 which fits with the ridged indentation 98 formed into the bracket 84 (FIG. 9). A magnet 100 shown in exploded view in FIG. 8 and shown in assembled position in FIG. 7 is located in the ring 96. In some infusion pumps, a magnet is used as part of a switch which controls pump operation. When the pump door is closed, the door-mounted magnet would active a switch located internally to the pump which would then enable pump operation. When the pump door is open, the loss of the magnetic field from the magnet would allow the magnetically-activated switch to open and operation of the pump would be prevented. Mounting the magnet 100 in the ring 96 and securing it in the ring with the bracket 84 in accordance with this aspect of the invention provides an improved magnetic switch device.

In prior techniques, the magnet would be held in position on the door with adhesive. Two main concerns arose with this technique. The first was that should the adhesive fail, the magnet would become detached from the door and the switch could not be activated thus rendering the infusion pump 10 unusable until repaired. The second was related to the increase in effort required during manufacture to accurately locate the magnet so that when the door was closed, the magnet was properly located to activate the switch.

The combination of the bracket 84 and the raised ring 96 on the door 12 holds the magnet securely in the correct position and overcomes the prior difficulties described above.

Returning now to the discussion of locating door parts, the bracket 84 is guided into correct location on the door 12 at several points. The protrusions/slots 92/94 and the raised/indented ring 96/98 both guide the bracket to the correct location. The retractor arm 74 is likewise accurately located by several points including the slots 90. At the other end, the bracket 84 includes a slot 102 for sliding over the door 12 at a notched area 104. It should also be noted that the bottom of the bracket 84 (FIG. 9) includes an indentation 106 to receive the retractor arm 74 so that the bracket 84 mounts flatly on the door 12. After assembly, the bracket 84 is welded to the access door 12 locking all components in place. Features on the slot edges facilitate welding.

FIG. 8 shows the block 76 being formed as part of the bracket 84. Additionally, the retractor arm 74 may be formed of spring steel with an injection molded end cap in which is formed the hook having the rounded outer surface 86 and the flat hook inner surface for engaging the second side of the lever handle 58. In another embodiment, the hook and block can be combined into a single component. A further feature of the bracket 84 design is that it will interfere with door closing if the valve 32 is not properly installed in the valve receptacle 42 in the infusion device. An upper ridge 108 will contact the valve if it is too high in the infusion device and prevent door closing. Similarly, the lower bracket ridge 110 and door ridges 112 will contact the valve 32 if it is lower than its proper position and prevent door closing.

BRIEF DESCRIPTION OF OPERATION

An administration set which includes the tubing 16 with the in-line valve 32 will normally be connected to the fluid reservoir 18 with the valve 32 in the flow position; i.e., lever rotated so that the passage through the valve is not blocked. Because of the lever-type design of the valve 32, the valve is manually operable as well as automatically operable. The administration set is primed with the fluid and the valve 32 set into the flow stop configuration by rotating the lever 58. The set may now be mounted in the pump 10. In the pump shown in the figures, the infusion engagement lever 36 would be moved to the left to engage the pressure plate 26 with the tubing 16 and the peristaltic fingers 28. Then as the door 12 of the pump is closed, the pushing block 76 of the automatic operation apparatus 72 will engage the first side 78 of the handle 58 and move it to the flow position. Before the block 76 engages the handle, the rounded portion 86 of the retractor arm 74 will have already encountered the ramp shape of the handle 58 and been forced over the handle to spring into place on the second side 82 of the handle. Because the valve 32 is located upstream of the peristaltic mechanism 24 and that pumping mechanism has previously been engaged with and is therefore occluding the tubing 16, no flow will occur as the block moves the handle to the flow position.

It should further be noted that the lever 36 of the peristaltic mechanism 24 is designed to protrude from the pump so that the door 12 of the pump 10 cannot be closed unless the lever 36 has been moved to engage the tubing with the pumping mechanism thereby occluding the tubing. Even if the door and lever are designed for interaction so that closing the door can also cause the pumping mechanism to engage the tubing, this engagement will occur before the valve being moved to the flow position. Therefore, the door cannot open the flow valve for fluid flow without first moving the pumping mechanism to the engaged position.

Similarly, the pumping mechanism lever 36 cannot be manipulated without first opening the access door 12. However when opening the access door 12, the retractor arm will engage the second side 82 of the handle 58 and pull the handle to rotate the channel 60 to the flow stop position. Flow through the tubing is then additionally blocked by the valve 32. The pumping mechanism may then be disengaged from occluding the tubing and free flow will not occur.

From the foregoing, it will be appreciated that the flow control system in accordance with the invention provides a more reliable system for preventing free flow. The flow and flow stop positions of a valve mounted to the pumping mechanism are selected in cooperation with the operational status of the pump. Additionally, the valve used is one which does not deform the tubing to obtain a flow stop condition but instead, provides a blocking device in the fluid flow passage to stop flow.

It will be apparent from the foregoing that, while particular forms of the invention have been illustrated and described, various modifications can be made without departing from the spirit and scope of the invention. Although embodiments of the invention have been described and illustrated, other embodiments are possible. For example, a flow controller as opposed to an infusion pump may be used. Other types of pumping mechanisms may be used which differ from a linear peristaltic mechanism. The invention may find application to a roller peristaltic mechanism for example. Similarly, a valve having a configuration other than with the handle shown may be used. Accordingly, it is not intended that the invention be limited, except as by the appended claims.

What is claimed is:

1. An apparatus for controlling the flow of fluid through a conduit which is operated on by a fluid infusion device to infuse a medical fluid to a patient, the apparatus comprising:

a valve disposed in line with and in fluid communication with the conduit such that fluid flowing through the conduit flows through the valve, the valve comprising:

a passage through which the fluid may flow;

a movable flow control member mounted in the valve and being movable into a first position in which the flow control member is disposed in the passage to block flow through the passage, and a second position in which the flow control member does not block flow through the passage;

an infusion engagement member having an engaged position at which it controls the fluid infusion device to engage the conduit for infusing fluid to the patient and having a disengaged position at which the infusion engagement member controls the fluid infusion device to be disengaged from the conduit; and a positioning device mounted to the fluid infusion device which controls the position of the flow control member and which interacts with the infusion engagement member so that the positioning device is restricted from setting the flow control member to the second position until after the infusion engagement member is in the engaged position.

2. The apparatus of claim 1 wherein the positioning device comprises a first member which moves the flow control member to the first position when the positioning device is moved in a first direction and a second member which moves the flow control member to the second position when the positioning device is moved in a second direction.

3. The apparatus of claim 2 wherein the first member of the positioning device comprises a retractor arm which engages the flow control member to move the flow control member to the first position when the positioning device is moved in the first direction.

4. The apparatus of claim 3 wherein the second member of the positioning device comprises a block which engages the flow control member to move the flow control member to the second position when the positioning device is moved in the second direction.

5. The apparatus of claim 2 further comprising an access door mounted to the infusion device, the access door having open and closed positions, wherein the positioning device is mounted to the access door such that when moving the access door from the open position to the closed position, the second member of the position device engages the flow control member to move the member into the second position and when moving the access door from the closed position to the open position, the first member of the positioning device engages the flow control member to move the member to the first position.

6. The apparatus of claim 4 further comprising:

an access door mounted to the infusion device, the access door having open and closed positions;

a handle attached to the movable flow control member which controls the position of the flow control member and has first and second positions corresponding to the first and second positions of the flow control member;

wherein the retractor arm is mounted to the access door and engages the handle to move the handle to the first position when the access door is moved from the closed to the open position; and wherein the block is mounted to the access door and engages the handle to move the handle to the second position when the access door is moved from the open to the closed position.

7. The apparatus of claim 2 wherein the flow control member further comprises a lever having first and second sides, the lever being attached to the movable flow control member to control the position of the flow control member, the lever having first and second positions corresponding to the first and second positions of the flow control member;

wherein the first member of the positioning device contacts the first side of the lever to move the lever to the first position and the second member of the positioning device contacts the second side of the lever to move the lever to the second position.

8. The apparatus of claim 7 wherein one of the surfaces of the lever is ramp shaped.

9. The apparatus of claim 8 wherein the side of the lever engaged by the second member of the positioning device is rounded at the tip of the lever.

10. The apparatus of claim 1 wherein the movable flow control member comprises a rotatable member inserted in the passage, the rotatable member having a channel which when aligned with the passage permits the flow of fluid through the valve and which when misaligned with the passage blocks the flow of fluid through the valve, the first position having the channel misaligned with the passage and the second position having the channel aligned with the passage.

11. The apparatus of claim 1 wherein the positioning device further interacts with the infusion engagement member so that the positioning device moves the flow control member to the first position before the infusion engagement member is moved to the disengaged position.

12. The apparatus of claim 11 wherein the positioning device comprises a first member which moves the flow control member to the first position when the positioning device is moved in a first direction and a second member which moves the flow control member to the second position when the positioning device is moved in a second direction.

13. The apparatus of claim 12 wherein the first member of the positioning device comprises a retractor arm which engages the flow control member to move the flow control member to the first position when the positioning device is moved in the first direction.

14. The apparatus of claim 13 wherein the second member of the positioning device comprises a block which engages the flow control member to move the flow control member to the second position when the positioning device is moved in the second direction.

15. The apparatus of claim 14 further comprising:

an access door mounted to the infusion device, the access door having open and closed positions;

a handle attached to the movable flow control member which controls the position of the flow control member and has first and second positions corresponding to the first and second positions of the flow control member;

wherein the retractor arm is mounted to the access door and moves the handle to the first position when the access door is moved from the closed to the open position; and wherein the block is mounted to the access door and moves the handle to the second position when the access door is moved from the open to the closed position.

16. The apparatus of claim 11 wherein the movable flow control member comprises a rotatable member inserted in the passage, the rotatable member having a channel which when aligned with the passage permits the flow of fluid through the valve and which when misaligned with the passage blocks the flow of fluid through the valve, the first position having the channel misaligned with the passage and the second position having the channel aligned with the passage.

17. The apparatus of claim 5 further comprising a magnet which is held in a predetermined position by the positioning device.

18. An apparatus for controlling the flow of fluid through a conduit which is operated on by a fluid infusion device to infuse a medical fluid to a patient, the apparatus comprising:
a valve disposed in line with and in fluid communication with the conduit such that fluid flowing through the conduit flows through the valve, the valve comprising:
a passage through which the fluid may flow;
a movable flow control member mounted in the valve and being movable into a first position in which the flow control member is disposed in the passage to block flow through the passage, and a second position in which the flow control member does not block flow through the passage, the flow control member comprising a handle which controls the position of the flow control member and has first and second positions corresponding to the first and second positions of the flow control member;
an infusion engagement member having an engaged position at which it controls the fluid infusion device to engage the conduit for infusing fluid to the patient and having a disengaged position at which the infusion engagement member controls the fluid infusion device to be disengaged from the conduit; and
a positioning device mounted to the fluid infusion device which controls the position of the flow control member by selectively positioning the handle in the first and second positions and which interacts with the infusion engagement member so that the positioning device is restricted from setting the flow control member to the second position until after the infusion engagement member is in the engaged position, and so that the positioning device moves the flow control member to the first position before the infusion engagement member can be moved to the disengaged position.

19. The apparatus of claim 18 wherein the positioning device comprises a retractor arm which engages the handle to move the flow control member to the first position when the positioning device is moved in a first direction.

20. The apparatus of claim 19 wherein the positioning device comprises a block which engages the handle to move the flow control member to the second position when the positioning device is moved in a second direction.

21. The apparatus of claim 18 further comprising an access door mounted to the infusion device, the access door having open and closed positions, wherein the positioning device is mounted to the access door such that when moving the access door from the open position to the closed position, the position device engages the handle to move the flow control member into the second position and when moving the access door from the closed position to the open position, the positioning device engages the handle to move the flow control member to the first position.

22. The apparatus of claim 20 further comprising:
an access door mounted to the infusion device, the access door having open and closed positions;
the handle comprises a lever attached to the movable flow control member which controls the position of the flow control member and has first and second positions corresponding to the first and second positions of the flow control member;
wherein the retractor arm is mounted on the access door and moves the handle to the first position when the access door is moved from the closed to the open position; and
wherein the block is mounted to the access door and moves the handle to the second position when the access door is moved from the open to the closed position.

23. The apparatus of claim 20 wherein:
the handle comprises a lever having first and second sides, the lever being attached to the flow control member to control the position of the flow control member and having first and second positions corresponding to the first and second positions of the flow control member;
the positioning device comprises a first member which contacts the first side of the lever to move the lever and the flow control member to the first position when the positioning device is moved in a first direction and the position device comprises a second member which contacts the second side of the lever to move the lever and the flow control member to the second position when the positioning device is moved in a second direction.

24. The apparatus of claim 23 wherein a surface of the lever is ramp shaped.

25. The apparatus of claim 23 wherein the side of the lever engaged by the second member of the positioning device and the end of the lever are rounded.

26. The apparatus of claim 18 wherein the movable flow control member comprises a rotatable member inserted in the passage, the rotatable member having a channel which when aligned with the passage permits the flow of fluid through the valve and which when misaligned with the passage blocks the flow of fluid through the valve, the first position having the channel misaligned with the passage and the second position having the channel aligned with the passage.

27. The apparatus of claim 21 further comprising a magnet which is held in a predetermined position by the positioning device.

28. An apparatus for controlling the flow of fluid through a conduit which is operated on by a fluid infusion device to infuse a medical fluid to a patient, the apparatus comprising:
a valve disposed in line with and in fluid communication with the conduit such that fluid flowing through the conduit flows through the valve, the valve comprising:
a passage through which the fluid may flow;
a rotatable member inserted in the passage, the rotatable member having a channel which when misaligned with the passage blocks the flow of fluid through the valve, and when aligned with the passage permits the flow of fluid through the valve, the first rotational member having a first position in which the channel is misaligned with the passage and a second position in which the channel is aligned with the passage, and wherein the flow control member further comprises a lever having first and second sides, the lever being attached to the movable flow control member to control the position of the flow control member, the lever having first and second positions corresponding to the first and second positions of the flow control member;

an infusion engagement member having an engaged position at which it controls the fluid infusion device to engage the conduit for infusing fluid to the patient and having a disengaged position at which the infusion engagement member controls the fluid infusion device to be disengaged from the conduit; and a positioning device mounted to the fluid infusion device which controls the position of the flow control member and which interacts with the infusion engagement member so that the positioning device is restricted from setting the flow control member to the second position until after the infusion engagement member is in the engaged position, and so that the positioning device moves the flow control member to the first position before the infusion engagement member is moved to the disengaged position, the positioning device comprising first and second members wherein the first member contacts the first side of the lever to move the lever to the first position when the positioning device is moved in a first direction and the second member contacts the second side of the lever to move the lever to the second position when the positioning device is moved in a second direction.

* * * * *